United States Patent
Zhao et al.

(10) Patent No.: US 12,420,114 B2
(45) Date of Patent: Sep. 23, 2025

(54) METHOD FOR GENERATING TREATMENT PLAN, COMPUTER DEVICE, AND STORAGE MEDIUM

(71) Applicant: OUR UNITED CORPORATION, Xi'an (CN)

(72) Inventors: Xikang Zhao, Xi'an (CN); Yipeng Jing, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 223 days.

(21) Appl. No.: 18/454,344

(22) Filed: Aug. 23, 2023

(65) Prior Publication Data

US 2025/0065150 A1  Feb. 27, 2025

(30) Foreign Application Priority Data

Jun. 29, 2022  (CN) .......................... 202210756573.1

(51) Int. Cl.
*A61N 5/10* (2006.01)
*G16H 20/40* (2018.01)

(52) U.S. Cl.
CPC ............. *A61N 5/1031* (2013.01); *A61N 5/10* (2013.01); *A61N 5/1001* (2013.01); *A61N 5/103* (2013.01); *A61N 5/1047* (2013.01); *A61N 5/1064* (2013.01); *A61N 5/1077* (2013.01); *G16H 20/40* (2018.01); *A61N 5/1039* (2013.01); *A61N 2005/1087* (2013.01); *A61N 2005/1089* (2013.01); *A61N 2005/109* (2013.01); *A61N 2005/1092* (2013.01)

(58) Field of Classification Search
CPC ........ A61N 5/10; A61N 5/1001; A61N 5/103; A61N 5/1031; A61N 5/1039; A61N 5/1047; A61N 5/1048; A61N 5/1077; A61N 2005/1087; A61N 2005/1089; A61N 2005/109; A61N 2005/1092; G16H 20/40

See application file for complete search history.

(56) References Cited

U.S. PATENT DOCUMENTS

2017/0157423 A1\* 6/2017 Bokrantz ............. A61N 5/1045

FOREIGN PATENT DOCUMENTS

WO    WO-2017063699 A1 \*  4/2017 ............. A61N 5/103

\* cited by examiner

*Primary Examiner* — Mark R Gaworecki
(74) *Attorney, Agent, or Firm* — Kolitch Romano Dascenzo Gates LLC

(57) ABSTRACT

Provided is a method for generating an arc treatment plan. The method for generating the arc treatment plan includes: generating a plurality of sub-regions by partitioning a region of interest based on an irradiation duration corresponding to the region of interest in a target volume; and generating the arc treatment plan for the target volume based on the plurality of sub-regions and irradiation durations corresponding to the plurality of sub-regions; wherein the irradiation durations corresponding to the plurality of sub-regions are all less than or equal to a predetermined value, a sum of the irradiation durations corresponding to the plurality of sub-regions is equal to an irradiation duration corresponding to the region of interest, and irradiation positions corresponding to the plurality of sub-regions are the same as an irradiation position corresponding to the region of interest.

20 Claims, 2 Drawing Sheets

METHOD FOR GENERATING TREATMENT PLAN, COMPUTER DEVICE, AND STORAGE MEDIUM

CROSS-REFERENCE TO RELATED APPLICATION

This application is based on and claims priority to Chinese Patent Application No. 202210756573.1, filed on Jun. 29, 2022, and entitled "ARCING TREATMENT PLAN GENERATION METHOD, COMPUTER EQUIPMENT AND STORAGE MEDIUM," the disclosure of which is herein incorporated by reference in its entirety.

TECHNICAL FIELD

The present disclosure relates to the field of radiation therapy technologies, and in particular, to a method for generating an arc treatment plan, a computer device, and a storage medium.

BACKGROUND

Radiation therapy is a common form of tumor treatment, and in the radiation therapy, tumor lesions are killed using high-energy radiations generated by a radiation device.

Generally, in performing the radiation treatment on a tumor of a patient, a radiation treatment plan is made first based on the tumor of the patient, and then a desired dose of radiation is applied to the tumor of the patient based on the radiation treatment plan by the radiation device to treat the tumor of the patient.

In arc irradiation (as a radiation treatment manner), a radiation source is in an arc rotation around an iso-center of the radiation device, and the radiations run through healthy issues in an unfixed path. Thus, irradiation doses of the healthy tissues are more dispersive, the healthy issues are protected, and iso-center focuses are irradiated with a maximum dose.

A treatment plan of arc irradiation requires to achieve delivery of a prescription dose to the focus when the arc is completed. In the case that a prescription dose of a target region or a target point is great in the treatment plan, the radiation device rotates at a minimum rotation speed, when delivery of a desirable dose cannot be achieved within an arc range, the treatment plan cannot be performed by the radiation device. In this case, the treatment plan maker requires to modify the treatment plan by adjusting a desired dose, a weight, and other parameters of the target region or the target point until the treatment plan meets quality requirements and are performable.

SUMMARY

Embodiments of the present disclosure provide a method for generating an arc treatment plan, a computer device, and a storage medium.

In some embodiments of the present disclosure, a method for generating an arc treatment plan is provided. The method includes:
generating a plurality of sub-regions by partitioning a region of interest based on an irradiation duration corresponding to the region of interest in a target volume; and
generating the arc treatment plan for the target volume based on the plurality of sub-regions and irradiation durations corresponding to the plurality of sub-regions;
wherein the irradiation duration corresponding to the region of interest is greater than a predetermined value, the irradiation durations corresponding to the plurality of sub-regions are all less than or equal to the predetermined value, a sum of the irradiation durations corresponding to the plurality of sub-regions is equal to the irradiation duration corresponding to the region of interest,
arc ranges corresponding to the plurality of sub-regions are the same as an arc range corresponding to the region of interest, and irradiation positions corresponding to the plurality of sub-regions are the same as an irradiation position corresponding to the region of interest.

In some embodiments, generating the plurality of sub-regions by partitioning the region of interest based on the irradiation duration corresponding to the region of interest in the target volume includes:
partitioning the region of interest into a target number of sub-regions with the same irradiation duration based on the irradiation duration corresponding to the region of interest; and
increasing the target number in response to the irradiation durations corresponding to the plurality of sub-regions being greater than the predetermined value, stopping the partitioning on the region of interest in response to the irradiation durations corresponding to the plurality of sub-regions being less than the predetermined value, and generating the plurality of sub-regions.

In some embodiments, an initial value of the target number is 2, and increasing the target number includes: increasing the target number by 1.

In some embodiments, generating the plurality of sub-regions by partitioning the region of interest based on the irradiation duration corresponding to the region of interest in the target volume includes:
partitioning the region of interest into a plurality of sub-regions with the same irradiation duration based on the irradiation duration corresponding to the region of interest and the predetermined value.

In some embodiments, upon generating the plurality of sub-regions by partitioning the region of interest based on the irradiation duration corresponding to the region of interest in the target volume, the method further includes:
ranking the plurality of sub-regions, and modifying the plurality of sub-regions, such that any two adjacent first sub-region and second sub-region are present in the plurality of sub-regions, wherein
an arc stop angle of the first sub-region is an arc start angle of the second sub-region, and an arc direction of the first sub-region is opposite to an arc direction of the second sub-region.

In some embodiments, generating the plurality of sub-regions by partitioning the region of interest based on the irradiation duration corresponding to the region of interest in the target volume includes: generating the plurality of sub-regions by partitioning the region of interest based on the irradiation duration corresponding to the region of interest in response to an instruction for duplicating the region of interest.

In some embodiments, the method further includes: determining whether the irradiation duration corresponding to the region of interest in the target volume is greater than the predetermined value; and generating the plurality of sub-regions by partitioning the region of interest based on the irradiation duration corresponding to the region of interest in the target volume includes: generating the plurality of sub-regions by partitioning the region of interest based on the irradiation duration corresponding to the region of interest in response to the irradiation duration corresponding to the region of interest being greater than the predetermined value.

In some embodiments, generating the plurality of sub-regions by partitioning the region of interest based on the irradiation duration corresponding to the region of interest in the target volume includes: generating the plurality of sub-regions by partitioning the region of interest based on the irradiation duration corresponding to the region of interest in response to a partition instruction.

In some embodiments, generating the plurality of sub-regions by partitioning the region of interest based on the irradiation duration corresponding to the region of interest in the target volume includes: generating the plurality of sub-regions by partitioning the region of interest based on the irradiation duration corresponding to the region of interest in response to a treatment plan accept instruction.

In some embodiments, radiation field sizes corresponding to the plurality of sub-regions are equal to a radiation field size corresponding to the region of interest.

In some embodiments, the predetermined value is determined based on a minimum rotation speed of a rotating gantry of a radiation device and the arc range corresponding to the region of interest.

In some embodiments of the present disclosure, a computer device is provided. The computer device includes: one or more processors; a memory; and one or more programs stored in the memory, wherein the one or more processors, when loading and running the one or more programs, are caused to perform the method for generating the arc treatment plan in the above embodiments.

In some embodiments of the present disclosure, a non-transitory computer readable storage medium storing computer programs is provided. The computer programs, when loaded and executed by a processor, cause the processor to perform the method for generating the arc treatment plan in the above embodiments.

In some embodiments of the present disclosure, a chip is provided. The chip includes: a processor and a communication interface that are coupled, wherein the processor, when loading and running programs or instructions, is caused to perform the method for generating the arc treatment plan in the above embodiments.

In some embodiments of the present disclosure, a computer program product including instructions is provided. The instructions, when loaded and executed by a processor, cause the processor to perform the method for generating the arc treatment plan in the above embodiments.

BRIEF DESCRIPTION OF DRAWINGS

For clearer descriptions of the technical solutions in the embodiments of the present disclosure, the following briefly introduces the accompanying drawings required for describing the embodiments. Apparently, the accompanying drawings in the following description show merely some embodiments of the present disclosure, and those skilled in the art may still derive other drawings from these accompanying drawings without creative efforts.

DETAILED DESCRIPTION

Figure 1:
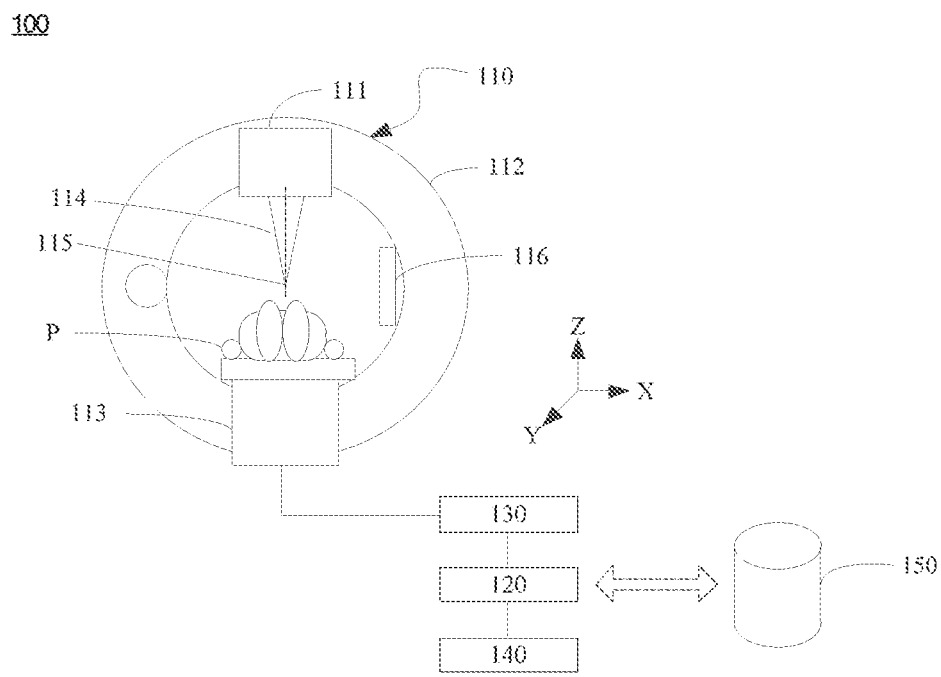
FIG. 1 is a schematic diagram of a scenario of a radiation device according to some embodiments of the present disclosure.

The technical solutions in the embodiments of the present disclosure will be clearly and completely described hereinafter with reference to the accompanying drawings in the embodiments of the present disclosure. Obviously, the described embodiments are merely some but not all embodiments of the present disclosure. Based on the embodiments of the present disclosure, all other embodiments derived by those skilled in the art without creative efforts shall fall within the protection scope of the present disclosure.

In the description of the present disclosure, it should be understood that orientation or positional relationships indicated by the terms "center," "longitudinal," "transverse," "length," "width," "thickness," "upper," "lower," "front," "back," "left," "right," "vertical," "horizontal," "top," "bottom," "inner," "outer," and the like are orientation or position relationship based on the accompanying drawings, and are merely intended to describe the present disclosure conveniently and simplify the description, rather than to indicate or imply that the referred apparatus or element must has a specific orientation or must be configured and operated at a specific orientation. Therefore, such terms should not be construed as limiting the present disclosure. Moreover, the terms "first," "second," and "third" are only for the purpose of description and should not be construed as indicating or implying relative importance or implicitly indicating the number of technical features indicated. Thus, the features defined by the terms "first," "second," and "third" may include one or more features explicitly or implicitly. In the description of the present disclosure, unless otherwise expressly defined, the term "a plurality of" means two or more.

In the present disclosure, the term "exemplary" is used to mean "being used as an example, for illustration, or explanation. Any embodiment described as being "exemplary" in the present disclosure may not necessarily be interpreted as more preferred or advantageous than other embodiments. The following description is given to implement and use the present disclosure by those skilled in the art. In the following description, details are shown for explanation. It should be understood that those of ordinary skill in the art can recognize that the present disclosure may also be implemented without using these specific details. In some embodiments, well-known structures and processes will not be elaborated in detail to avoid obscuring the description of the present disclosure by unnecessary details. Thus, the present disclosure is not intended to be limited to the shown embodiments, but should be consistent with the widest scope conforming to the principles and features disclosed herein.

It should be noted that as the method in the embodiments of the present disclosure is performed in a computer device, and processed objects of the computer device exist in the form of data or information, such as time, which is essentially time information. It can be understood that sizes, quantities, positions, and the like mentioned in subsequent embodiments are in the form of corresponding data for facilitating processing by the computer device, and specific details will not be described herein.

The present disclosure involves radiation technologies, and radiation beams for radiation include particle beams (for example, neutron beams, proton beams, electron beams, and the like), photon beams (for example, X-rays, gamma rays), or a combination thereof. The embodiments of the present disclosure provide a method for generating an arc treatment plan, a computer device, and a storage medium. The arc treatment plan cannot be performed by a radiation device as a rotation speed of a radiation source is not slow enough in the method for generating the arc treatment plan. In the technical solutions of the present disclosure, a target point or a target region in the arc treatment plan is partitioned, such that the radiation source can move back and forth within an arc range of the target point or the target region, and the arc treatment plan is performed by the radiation device.

FIG. 1 exemplarily shows a radiation device 100 according to some embodiments of the present disclosure. The radiation device 100 includes a radiation delivery apparatus 110, a master control system 120, a slave control system 130, a treatment planning system (TPS) 140, and a memory 150. In some embodiments, the radiation delivery apparatus 110, the master control system 120, the slave control system 130, the TPS 140, and the memory 150 are in wireless connection (for example, network connection) or wired connection, connected and/or communicated with each other in a combined manner.

In some embodiments, the radiation delivery apparatus 110 is an apparatus for delivering radiation for treatment. The radiation delivery apparatus 110 includes a radiation source 111, a rotating gantry 112, and a treatment bed 113.

The radiation source 111 is capable of generating or emitting a radiation beam 114. The radiation source 111 is a linear accelerator or a treatment head loaded with a radioactive isotope source (such as a cobalt-60 radioactive source). There may be one or more (such as two) radiation sources 111.

The rotating gantry 112 is configured to support the radiation source 111 and is capable of driving the radiation source 111 to rotate around a rotation axis 115. The rotation axis 115 is intersected with a central axis of the radiation beam 114 at an isocenter point.

The treatment bed 113 is configured to support a patient P, and capable of translating in one or more of three orthogonal directions (X, Y, and Z directions shown in FIG. 1). In some embodiments, the treatment bed 113 rotates around any one or more of X, Y, and Z axes.

A position of the radiation source 111 relative to the patient and an orientation of radiation beam 114 relative to the patient are achieved by controlling movements of the rotating gantry 112 and/or the treatment bed 113.

In some embodiments, the radiation delivery apparatus 110 includes an image guided apparatus 116 configured to provide a medical image for determining at least part (such as a region of interest) of the patient. In some embodiments, the image guided apparatus 116 is, for example, a computed tomography (CT) device, a cone-beam CT device, a positron emission computed tomography (PET) device, a volume CT device, a magnetic resonance imaging (MRI) device, or a combination thereof.

In some embodiments, the master control system 120 is configured to generate control instructions for one or more assemblies (such as the slave control system 130, the TPS 140, and/or the memory 150) of the radiation device 100. For example, the master control system 120 sends an instruction to the slave control system 130 to control the radiation delivery apparatus 110 to initiate an image guidance or treatment process. For example, the master control system 120 sends an instruction to the TPS 140 and acquires the treatment plan. In some embodiments, the instructions are input by the user (such as, a doctor) over a user interface of the master control system 120.

In some embodiments, the slave control system 130 is configured to control, in response to the control instruction generated by the master control system 120, the radiation delivery apparatus 110 to perform a corresponding action. For example, the slave control system 130 controls, in response to a setup instruction from the master control system 120, the movement of the treatment bed 113 of the radiation delivery apparatus 110 to complete setup. For example, the slave control system 130 controls, in response to a radiation delivery instruction from the master control system 120, the movement of the rotating gantry 112 of the radiation delivery apparatus 110 to achieve radiation delivery. For example, the slave control system 130 controls, in response to an image guidance instruction from the master control system 120, the image guided apparatus 116 of the radiation delivery apparatus 110 to perform the image guidance on the patient to generate the medical image of the patient.

In some embodiments, the TPS 140 is configured to determine the treatment plan based on at least part of objects (such as, a tumor) in a planned image of the patient (the planned image is an image of the patient acquired prior to treatment using an imaging apparatus) and/or an image acquired based on the image guided apparatus 116.

In some embodiments, both the master control system 120 and the TPS 140 are computer devices provided with graphical user interfaces (GUI). The computer device includes one or more processors, a memory, and one or more applications. For example, the one or more applications in the TPS 140 are stored in the memory, and the one or more processors, when loading and running the one or more applications, are caused to perform the method for generating the arc treatment plan in the present disclosure. In some embodiments, the graphical user interface of the TPS 140 is configured to interact with the user for making the treatment plan.

In some embodiments, the master control system 120 and the TPS 140 are independent servers, or a server network or server cluster composed of servers. For example, the computer device in the embodiments of the present disclosure includes, but is not limited to a computer, a network host, a single network server, a multi-network-server set, or a cloud server composed of a plurality of servers. The cloud server is composed of a large number of computers or network servers based on cloud computing.

In some embodiments, the master control system 120 and the TPS 140 are a general-purpose computer device or a special-purpose computer device. In the specific implementation, the computer device is a desktop computer, a portable computer, a network server, a personal digital assistant (PDA) computer, a mobile phone, a tablet computer, a wireless terminal device, a communication device, an embedded device, and the like, and the type of the computer device is not limited in the embodiments.

In some embodiments, the slave control system 130 is a computer device, and the computer device includes a processor, a storage device, an input/output (I/O), and a communication port. The processor 310 includes a microcontroller, a microprocessor, a reduced instruction set computer (RISC), an application specific integrated circuit (ASIC), an application specific instruction-set processor (ASIP), a central processing unit (CPU), a graphics processing unit (GPU), a physical processing unit (PPU), a single-chip microcomputer, a digital signal processor (DSP), a field programmable gate array (FPGA), an advanced reduced instruction set machine (ARM), a programmable logic devices (PLD), any circuit or processor capable of achieving at least one function, or any combination thereof.

For the radiation device 100 in the embodiments, in performing the radiation therapy, the master control system 120 acquires the treatment plan for tumor treatment of the patient from the TPS 140, and issues the acquired treatment plan and the control instructions to the slave control system 130. The slave control system 130 controls, based on treatment plan information and the control instructions, the radiation delivery apparatus 110 to deliver the radiation therapy to the tumor of the patient.

In some embodiments, the radiation device 100 further includes one or more other computer devices capable of processing data, for example, an oncology information system (OIS). The OIS is configured to schedule the treatment plan for the patients and store treatment data (such as image data of the patient, treatment plan data of the patient, radiation delivery information of the patient, and the like).

The memory 150 stores data, instructions, and/or any other information. In some embodiments, the memory 150 stores data acquired from the TPS 140. In some embodiments, the memory 150 stores data and/or instructions used by the master control system 120 to perform the exemplary method in the present disclosure. In some embodiments, the memory 150 includes a high-capacity memory, a removable memory, a volatile read-write memory, a read-only memory (ROM), or any combination thereof. The exemplary high-capacity memory includes disks, optical disks, solid-state drives, and the like. The exemplary removable memory includes flash drives, floppy disks, optical disks, memory cards, compressed disks, magnetic tapes, and the like. The exemplary volatile read-write memory includes a random access memory (RAM). The exemplary RAM includes a dynamic random access memory (DRAM), a double data rate synchronous dynamic random-access memory (DDR SDRAM), a static random access memory (SRAM), a thyristor random access memory (T-RAM), a zero-capacitor random access memory (Z-RAM), and the like. The exemplary ROM includes a mask ROM (MROM), a programmable ROM (PROM), an erasable programmable ROM (EPROM), an electrically erasable programmable ROM (EEPROM), a compact disc ROM (CD-ROM), a digital multifunctional disc ROM, and the like. In some embodiments, the memory 150 is implemented on a cloud platform. For example, the cloud platform includes private clouds, public clouds, hybrid clouds, community clouds, distributed clouds, internal clouds, multi-layer clouds, or any combination thereof.

In some embodiments, the memory 150 is connected to a network to communicate with one or more assemblies (such as the master control system 120, the TPS 140, and the OIS) of the radiation device 100. The one or more assemblies of the radiation device 100 access data or instructions stored in the memory 150 over a network. In some embodiments, the memory 150 is directly connected to or communicated with one or more assemblies (such as the master control system 120, the TPS 140, and the OIS) of the radiation device 100. In some embodiments, the memory 150 is part of the master control system 120, the TPS 140, and the OIS.

It should be noted that the schematic diagram of the scenario of the radiation device shown in FIG. 1 is only an example. The radiation device and the scenario described in the embodiments of the present disclosure are for clearer description of the technical solutions in the embodiments of the present disclosure, and do not constitute a limitation to the technical solutions in the embodiments of the present disclosure. Those of ordinary skill in the art may know that with the evolution of the radiation device and the emergence of new service scenarios, the technical solution in the embodiments of the present disclosure is also applicable to similar technical problems.

Firstly, the embodiments of the present disclosure provide a method for generating an arc treatment plan. An execution subject of the method for generating the arc treatment plan is the processor in the computer device. The method for generating the arc treatment plan includes:

generating a plurality of sub-regions by partitioning a region of interest in a target volume, and generating an arc treatment plan for the target volume based on the plurality of sub-regions and irradiation durations corresponding to the plurality of sub-regions. The irradiation duration corresponding to the region of interest is greater than a predetermined value, the irradiation durations corresponding to the plurality of sub-regions are all less than or equal to the predetermined value, a sum of the irradiation durations corresponding to the plurality of sub-regions is equal to the irradiation duration corresponding to the region of interest, arc ranges corresponding to the plurality of sub-regions are the same as an arc range corresponding to the region of interest, and irradiation positions corresponding to the plurality of sub-regions are the same as an irradiation position corresponding to the region of interest.

In the embodiments of the present disclosure, the target volume refers to a target region, for example, a tumor or part of a tumor, and the region of interest refers to the target region or part of a target region (for example, a target point).

Generally, in making the treatment plan, the target region and the organ at risk are outlined in a treatment plan system based on image data of the patient, and a dosimetrist, a doctor, or a medical worker determines a radiation dose to be supplied to the target region and any maximum dose accepted by the organ at risk. Upon determination of the radiation dose of the target region and the organ at risk, a process also referred to as a forward planning is performed. That is, a target point is determined in the target region, and collimator parameters of the target point, an arc range, and a weight of the target point are set to output a treatment plan capable of achieving desirable dose distribution. Upon determination of the radiation dose of the target region and the organ at risk, a process also referred to as a backward planning is performed to determine one or more treatment plan parameters capable of achieving desirable dose distribution.

The treatment plan acquired in the above planning may be not performed due to an effect of a rotation speed of a rotating gantry of a radiation device. For example, in the case that an irradiation duration planned in the plan is longer, the radiation device cannot complete delivery of the desirable dose within an arc range planned in the plan. In this case, the treatment plan requires to be modified, such that (1) the treatment plan can be performed by the radiation device, and (2) the desirable dose distribution can be achieved. A process of modifying the treatment plan is long and time-consumed for meeting the above requirements in (1) and (2).

Thus, a method for generating an arc treatment plan is provided in the present disclosure. In the method, the arc treatment plan is performed by partitioning the target point or the target region that cannot be performed. In detail, the target point or the target region that cannot be performed is partitioned, such that the radiation source of the radiation device can move back and forth within the arc range, and the delivery of the desirable dose is achieved.

Figure 2:
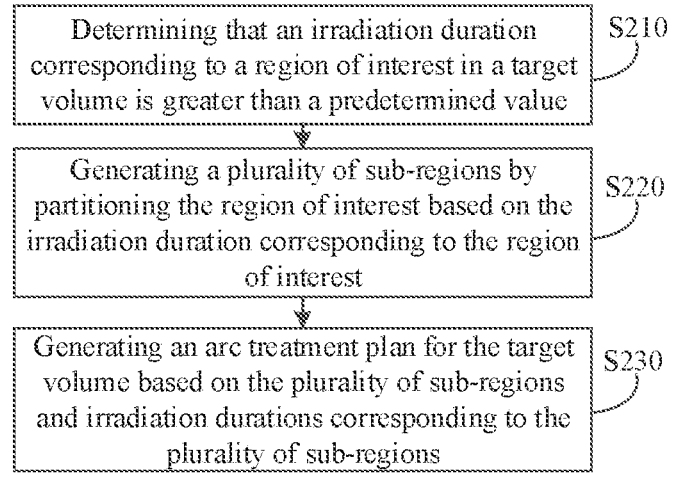
FIG. 2 is a schematic flowchart of a method for generating an arc treatment plan according to some embodiments of the present disclosure.

FIG. 2 is a schematic flowchart of a method for generating an arc treatment plan according to some embodiments of the present disclosure. As shown in FIG. 2, the method for generating the arc treatment plan includes the following S210 to S230.

In S210, an irradiation duration corresponding to a region of interest in a target volume being greater than a predetermined value is determined.

A processor in a computer device performing the method for generating the arc treatment plan in the present disclosure determines that the irradiation duration corresponding to the region of interest in the target volume is greater than the predetermined value.

In the embodiments of the present disclosure, the irradiation duration corresponding to the region of interest is correlated with a prescription dose of the target volume and an output factor of supplying radiation to the target volume, and is determined by the treatment plan system.

In the embodiments of the present disclosure, the predetermined value is a time value, and is determined by the treatment plan system based on a minimum rotation speed of a rotating gantry of the radiation device and the arc range (an arc length) corresponding to the region of interest. The predetermined value refers to a maximum irradiation capacity of the radiation device within the arc range corresponding to the region of interest, that is a maximum irradiation duration of the radiation device within the arc range corresponding to the region of interest. Predetermined values are different for regions of interest with different arc lengths.

In some embodiments, the processor in the computer device performing the method for generating the arc treatment plan in the present disclosure determines whether the irradiation duration corresponding to the region of interest in the target volume is greater than the predetermined value in making the treatment plan. For example, in a forward planning process, the determination of whether an irradiation duration corresponding to a target point is greater than the predetermined value is performed each time the target point is set. In some embodiments, the determination of whether the irradiation duration corresponding to the region of interest in the target volume is greater than the predetermined value is performed upon completion of making the treatment plan. For example, the determination of whether an irradiation duration corresponding to a target region is greater than the predetermined value is performed upon a backward planning process.

In S220, a plurality of sub-regions are generated by partitioning the region of interest based on the irradiation duration corresponding to the region of interest in the target volume.

The processor in the computer device performing the method for generating the arc treatment plan in the present disclosure generates the plurality of sub-regions by partitioning the region of interest based on the irradiation duration corresponding to the region of interest in the target volume upon determination of the irradiation duration corresponding to the region of interest in the target volume being greater than the predetermined value.

In the embodiments of the present disclosure, the irradiation durations corresponding to the plurality of sub-regions are all less than or equal to the predetermined value, a sum of the irradiation durations corresponding to the plurality of sub-regions is equal to the irradiation duration corresponding to the region of interest, and arc ranges corresponding to the plurality of sub-regions are the same as an arc range corresponding to the region of interest. As such, the radiation device can complete the delivery of the desirable radiation dose to the region of interest within the original arc range.

For example, in the case that an arc range corresponding to a target point in the target region ranges from 0° to 60°, an irradiation duration corresponding to the target point is six minutes, and a minimum rotation speed of a rotating gantry of a radiation device is 1°/s, thus for the target point, a maximum irradiation duration that can be performed by the radiation device is 60 s. The target point needs to be partitioned as the capacity of the radiation device is exceeded.

As the irradiation duration corresponding to the target point (that is, the region of interest) is six minutes, the target point is partitioned into at least six target points (that is, sub-regions), for example, six target points, eight target points, or more target points. The irradiation durations of the partitioned target points are less than or equal to 60 s, and less than or equal to the maximum irradiation duration of the radiation device within the original arc range. In addition, a sum of the irradiation durations of the partitioned target points is equal to the duration of the original target point, arc ranges of the partitioned target points are the same as an arc range of the original target point, and irradiation positions of the partitioned target points are the same as an irradiation position of the original target point. As such, the delivery of the radiation to the original target point is achieved on the premise that the original arc range is not changed.

A maximum number of target points partitioned from the original target point is correlated with the maximum rotation speed of the rotating gantry of the radiation device. Generally, a minimum number of the target points in which the radiation device achieves the delivery of the desirable radiation dose to the target point within the original arc range is selected, such that a duration for generating the arc treatment plan is shortened.

It should be understood that in some embodiments, the processor in the computer device does not require to perform the above processes of S210. That is, the processor does not require to detect and determine whether the irradiation duration corresponding to the region of interest in the target volume is greater than the predetermined value. For example, the processor directly performs the process of S220 based on a received instruction of the user.

In S230, the arc treatment plan for the target volume is generated based on the plurality of sub-regions and irradiation durations corresponding to the plurality of sub-regions.

The processor in the computer device performing the method for generating the arc treatment plan in the present disclosure saves the plurality of sub-regions upon generation of the plurality of sub-regions. In addition, the processor generates the arc treatment plan for the target volume based on the plurality of sub-regions and the irradiation durations corresponding to the plurality of sub-regions, such that the radiation device achieves the delivery of the radiation.

In the method for generating the arc treatment plan, the target region or the target point that cannot be performed by the radiation device due to a long irradiation duration is partitioned, such that the target region or the target point can be performed to avoid modifying the treatment plan by the maker of the treatment plan by adjusting the dose, the weight, and other parameters of the target region or the target point, and the duration for planning the arc treatment plan is shortened.

In some embodiments, radiation field sizes corresponding to the plurality of generated sub-regions are equal to a radiation field size corresponding to the region of interest, such that the treatment plan is performed on the premise that the quality of the original arc treatment plan is not changed.

For example, for a gamma knife radiation device, the radiation field size is adjusted by switching collimators with different apertures. Thus, the radiation field sizes corresponding to the plurality of generated sub-regions being equal refers to that sizes of the collimators corresponding to the plurality of generated sub-regions are equal. For an electron linear accelerator device, the radiation field size is adjusted by adjusting positions of leaves of the multi-leaf collimator.

In some embodiments, the irradiation durations corresponding to the plurality of sub-regions are equal. In some embodiments, the irradiation durations corresponding to the plurality of generated sub-regions are not equal. In the case that the irradiation durations corresponding to the plurality of sub-regions are equal, the partitioning process of the region of interest is simplified, and the duration for generating the arc treatment plan is further shortened.

In some embodiments, the region of interest is partitioned in the process of planning the arc treatment plan. In some embodiments, the region of interest is partitioned upon completion of planning the arc treatment plan.

In the case that the region of interest is partitioned in the process of planning the arc treatment plan:

In some embodiments, the processor in the computer device performing the method for generating the arc treatment plan in the present disclosure generates the plurality of sub-regions by partitioning the region of interest based on the irradiation duration corresponding to the region of interest in response to an instruction for duplicating the region of interest.

For example, the user adds a region of interest by triggering a button for duplicating the region of interest on an interactive interface of the computer device performing the method for generating the arc treatment plan in the present disclosure, such that a partition instruction is issued. The partition instruction is configured to instruct the processor in the computer device performing the method for generating the arc treatment plan in the present disclosure to partition the region of interest based on the irradiation duration corresponding to the region of interest, such that a sum of an irradiation duration corresponding to the partitioned original region of interest and an irradiation duration corresponding to the newly added region of interest is equal to the irradiation duration corresponding to the original region of interest prior to partitioning, an arc range corresponding to the partitioned original region of interest and an arc range corresponding to the newly added region of interest are the same as the arc range corresponding to the original region of interest prior to partitioning, and an irradiation position corresponding to the partitioned original region of interest and an irradiation position corresponding to the newly added region of interest are the same as the irradiation position corresponding to the original region of interest prior to partitioning. In this case, the partitioned original region of interest and the newly added region of interest are two sub-regions. In the case that the generated two sub-regions further include a region with an irradiation duration being greater than the predetermined value, the user continues to trigger the button for duplicating the region of interest, and the original region of interest is partitioned into three sub-regions, and the process is repeated until irradiation durations corresponding to all generated sub-regions are less than the predetermined value.

In the embodiments, the region of interest is partitioned in response to the button for duplicating the region of interest of the user, such that the treatment plan system has a manual partition function, and the user can partition manually.

In some embodiments, the processor in the computer device performing the method for generating the arc treatment plan in the present disclosure generates the plurality of sub-regions by partitioning the region of interest based on the irradiation duration corresponding to the region of interest in response to a partition instruction of the user.

For example, the user triggers a button for partitioning the region of interest on the interactive interface of the computer device performing the method for generating the arc treatment plan in the present disclosure, such that the partition instruction is issued. The partition instruction is configured to instruct the processor in the computer device performing the method for generating the arc treatment plan in the present disclosure to automatically partition the region of interest based on the irradiation duration corresponding to the region of interest, such that the plurality of sub-regions are generated. In this case, the irradiation durations corresponding to the plurality of generated sub-regions are all less than or equal to the predetermined value, a sum of the irradiation durations corresponding to the plurality of sub-regions is equal to the irradiation duration corresponding to the region of interest, the arc ranges corresponding to the plurality of sub-regions are the same as the arc range corresponding to the region of interest, and the irradiation positions corresponding to the plurality of sub-regions are the same as the irradiation position corresponding to the region of interest.

In the embodiments, the region of interest is automatically partitioned in response to the partition instruction of the user, such that the speed of partitioning the region of interest is improved, and the duration of generating the arc treatment plan is shortened.

In the case that the region of interest is partitioned upon completion of planning the arc treatment plan:

In some embodiments, the processor in the computer device performing the method for generating the arc treatment plan in the present disclosure generates the plurality of sub-regions by partitioning the region of interest based on the irradiation duration corresponding to the region of interest in response to a treatment plan accept instruction.

For example, upon completion of planning the arc treatment plan, the user triggers a treatment plan accepting button on the interactive interface of the computer device performing the method for generating the arc treatment plan in the present disclosure, such that the treatment plan accept instruction is issued. The processor in the computer device performing the method for generating the arc treatment plan in the present disclosure automatically partitions the region of interest upon receipt of the treatment plan accept instruction, such that the plurality of sub-regions are generated. In this case, the irradiation durations corresponding to the plurality of generated sub-regions are all less than or equal to the predetermined value, a sum of the irradiation durations corresponding to the plurality of sub-regions is equal to the irradiation duration corresponding to the region of interest, the arc ranges corresponding to the plurality of sub-regions are the same as the arc range corresponding to the region of interest, and the irradiation positions corresponding to the plurality of sub-regions are the same as the irradiation position corresponding to the region of interest.

In the embodiments, the region of interest is automatically partitioned in response to the treatment plan accept instruction of the user to avoid that the generated treatment plan cannot be performed by the radiation device.

In some embodiments, generating the plurality of sub-regions by partitioning the region of interest based on the irradiation duration corresponding to the region of interest includes: partitioning the region of interest into a plurality of sub-regions with equal irradiation durations based on the irradiation duration corresponding to the region of interest step-by-step, stopping the partitioning on the region of interest in response to the irradiation durations corresponding to the plurality of sub-regions being less than the predetermined value, and generating the plurality of sub-regions.

In some embodiments, partitioning the region of interest step-by-step includes: partitioning the region of interest into a target number of sub-regions with the same irradiation duration, and increasing the target number and re-partitioning the region of interest in response to the irradiation durations corresponding to the plurality of sub-regions being greater than the predetermined value until the irradiation durations corresponding to the plurality of sub-regions are all less than the predetermined value. An initial value of the target number is an integer greater than 1, for example, 2. In the case that the processor in the computer device performing the method for generating the arc treatment plan in the present disclosure increases the target number, the target number may be increased by a fixed number, for example, 1.

In some embodiments, the processor in the computer device performing the method for generating the arc treatment plan in the present disclosure partitions the region of interest into two sub-regions with the same irradiation duration based on the irradiation duration corresponding to the region of interest, and determines whether the irradiation durations corresponding to the two sub-regions are greater than the predetermined value. In the case that the irradiation durations corresponding to the two sub-regions are less than or equal to the predetermined value, the partitioning on the region of interest is stopped, and two sub-regions are generated. In the case that the irradiation durations corresponding to the two sub-regions are greater than the predetermined value, the region of interest is continued to be partitioned into three sub-regions with the same irradiation duration, and whether the irradiation durations corresponding to the three sub-regions are greater than the predetermined value is determined. In the case that the irradiation durations corresponding to the three sub-regions are greater than the predetermined value, the region of interest is partitioned into four, five, or other number of sub-regions, the partitioning on the region of interest is stopped in response to the irradiation durations corresponding to the sub-regions being less than the predetermined value, and the plurality of sub-regions are generated.

In some embodiments, generating the plurality of sub-regions by partitioning the region of interest based on the irradiation duration corresponding to the region of interest includes: partitioning the region of interest into a plurality of sub-regions with the same irradiation duration based on the irradiation duration corresponding to the region of interest and the predetermined value.

The processor in the computer device performing the method for generating the arc treatment plan in the present disclosure calculates a number of sub-regions to be partitioned based on the irradiation duration corresponding to the region of interest and the predetermined value, and partitions the region of interest into the corresponding number of sub-regions with the same irradiation duration based on the number.

In the embodiments of the present disclosure, the plurality of sub-regions are generated by partitioning the region of interest based on the irradiation duration corresponding to the region of interest, and the arc ranges corresponding to the plurality of sub-regions are the same as the arc range corresponding to the region of interest. For example, the arc range corresponding to the region of interest ranges from 0° to 180°, and the arc ranges corresponding to the plurality of sub-regions also range from 0° to 180°. In the case that the radiation device performs the arc irradiation, an arc start angle and an arc stop angle of each sub-region should be determined. In the case that arc start angles of the plurality of sub-regions are all 0°, and arc stop angles of the plurality of sub-regions are all 180°, when the radiation device performs the arc irradiation, the radiation source stops emitting the beams each time the arc irradiation of one sub-region is completed, and the arc irradiation of a next sub-region is started upon idle rotation of the radiation source by 180° and returning of the radiation source to 0°, such that a duration of the radiation treatment is increased.

Figure 3:
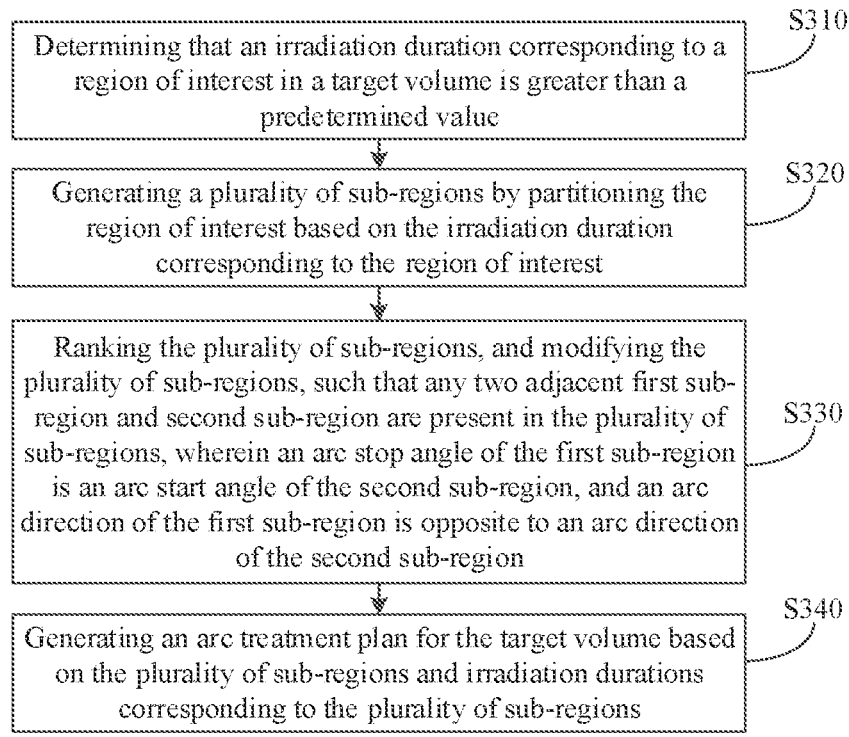
FIG. 3 is a schematic flowchart of a method for generating an arc treatment plan according to some embodiments of the present disclosure.

For shortening of the duration of the radiation treatment, FIG. 3 is a schematic flowchart of a method for generating an arc treatment plan according to some embodiments of the present disclosure. As shown in FIG. 3, a ranking process and a modifying process for the plurality of sub-regions are added after S220 in the embodiments shown in FIG. 2 in the method for generating the arc treatment plan. The ranking process and the modifying process include S310 to S340. In the embodiments, S310, S320, and S340 are the same as S210, S220, and S230 in the embodiments shown in FIG. 2, which are not repeated herein.

As shown in S330 in FIG. 3, in the embodiments, upon generation of the plurality of sub-regions by partitioning the region of interest, the plurality of sub-regions are ranked and modified, such that any two adjacent first sub-region and second sub-region are present in the plurality of sub-regions. An arc stop angle of the first sub-region is an arc start angle of the second sub-region, and an arc direction of the first sub-region is opposite to an arc direction of the second sub-region.

By taking the arc ranges being from 0° to 180°, and three sub-regions being generated as an example, the processor in the computer device performing the method for generating the arc treatment plan in the present disclosure ranks and modifies the three sub-regions, such that an arc start angle of a first sub-region is 0°, an arc stop angle of the first sub-region is 180°, an arc direction of the first sub-region is clockwise, an arc start angle of a second sub-region is 180°, an arc stop angle of the second sub-region is 0°, an arc direction of the second sub-region is counterclockwise, an arc start angle of a third sub-region is 0°, an arc stop angle of the third sub-region is 180°, and an arc direction of the third sub-region is clockwise.

As such, in the case that the radiation device performs the arc irradiation, the radiation source moves from 0° to 180° in a clockwise direction, such that the arc irradiation of the first sub-region is completed. Then, the radiation source does not require to suspend emitting beams, and the radiation source moves in an inverse direction, such that the arc irradiation of the second sub-region is started. That is, the radiation source emits beams continuously, and moves from 180° to 0° in a counterclockwise direction, such that the arc irradiation of the second sub-region is completed. Then, the radiation source emits beams continuously, and moves from 0° to 180° in a clockwise direction, such that the arc irradiation of the third sub-region is completed.

As an arc start angle of a next sub-region is an arc stop angle of a previous sub-region, and an arc direction of the next sub-region is opposite to an arc direction of the previous sub-region, upon completion of the irradiation of one sub-region, the radiation source does not require to suspend emitting beams and idly rotate, and irradiation of the next radiation source directly starts, such that the duration of the radiation treatment is shortened.

In the method for generating the arc treatment plan, the target region or the target point that cannot be performed by the radiation device due to a long irradiation duration is performed to avoid modifying the treatment plan by the maker of the treatment plan by adjusting the dose, the weight, and other parameters of the target region or the target point, such that the duration for planning the arc treatment plan is shortened.

Figure 4:
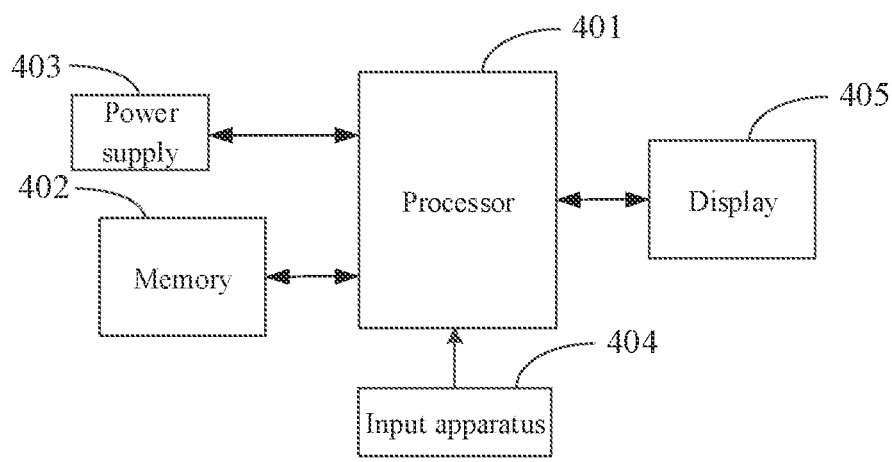
FIG. 4 is a schematic structural diagram of a computer device according to some embodiments of the present disclosure.

Some embodiments of the present disclosure further provide a computer device. The computer device includes: one or more processors; a memory; and one or more programs, wherein the one or more programs are stored in the memory, and the processor, when loading and running the one or more programs, is caused to perform the method for generating the arc treatment plan in any one of the above embodiments. As shown in FIG. 4, FIG. 4 shows a structural schematic diagram of a computer device in the embodiments of the present disclosure. The details are as follows.

The computer device includes assemblies, such as a processor 401 having one or more processing cores, a memory 402 of one or more computer-readable storage medias, a power supply 403, and an input apparatus 404. It can be understood by those skilled in the art that the computer device structure shown in FIG. 4 does not constitute a limitation to the computer device. The computer device includes more or fewer assemblies than those shown in the drawing, or combines some components, or uses different component arrangements.

The processor 401 is a control center of the computer device, and connects various parts of the entire computer device through various interfaces and lines. By running or executing software programs and/or modules stored in the memory 402 and invoking data stored in the memory 402, various functions and processing data of the computer device are implemented, such that the computer device is monitored.

In some embodiments, the processor 401 includes one or more processing cores. In some embodiments, the processor 401 is integrated as an application processor and a modulation and demodulation processor. The application processor mainly processes an operating system, a user interface, an application, and the like, and the modulation and demodulation processor mainly processes wireless communication. It can be understood that the above modulation and demodulation processor may also not be integrated into the processor 401.

The memory 402 is configured to store software programs and modules, and the processor 401 executes various functional applications and data processing by running the software programs and the modules stored in the memory 402. The memory 402 mainly includes a program storage region and a data storage region. The program storage region stores the operating system, an application required for at least one function (such as a sound playing function and an image playing function), and the like. The data storage region stores data created based on the use of the computer device, and the like. In addition, the memory 402 includes a high-speed random access memory and a non-volatile memory, such as at least one of a disk storage device, a flash memory device, or other volatile solid-state storage devices. Correspondingly, the memory 402 also includes a memory controller to provide access to the memory 402 by the processor 401.

The computer device also includes the power supply 403 that supplies power to various assemblies. In some embodiments, the power supply 403 is logically connected to the processor 401 through a power supply management system, such that the functions, such as management of charging, discharging, and power consumption are achieved through the power supply management system. The power supply 403 further includes one or more direct current or alternating current power supplies, a recharging systems, a power failure detection circuit, a power converter or an inverter, a power status indicator, and any other assemblies.

The computer device also includes an input apparatus 404. The input apparatus 404 is configured to receive input digital or character information, and generate keyboard, mouse, joystick, optical, or trackball signal input related to user settings and function control.

Although not shown, the computer device further includes a display apparatus 405. The display apparatus 405 is a display, and thus will not be repeated herein. Specifically, in the embodiments, the processor 401 in the computer device loads, according to the following instructions, executable files corresponding to one or more programs into the memory 402, and the processor 401 runs the programs stored in the memory 402 to achieve various functions as follows:

generating a plurality of sub-regions by partitioning a region of interest based on an irradiation duration corresponding to the region of interest in a target volume; and generating the arc treatment plan for the target volume based on the plurality of sub-regions and irradiation durations corresponding to the plurality of sub-regions;

wherein the irradiation duration corresponding to the region of interest is greater than a predetermined value, the irradiation durations corresponding to the plurality of sub-regions are all less than or equal to the predetermined value, a sum of the irradiation durations corresponding to the plurality of sub-regions is equal to the irradiation duration corresponding to the region of interest, arc ranges corresponding to the plurality of sub-regions are the same as an arc range corresponding to the region of interest, and irradiation positions corresponding to the plurality of sub-regions are the same as an irradiation position corresponding to the region of interest.

Those of ordinary skill in the art may understand that all or part of the processes in the various methods of the above embodiments can be performed by instructions, or by controlling related hardware through instructions. The instructions may be stored in a computer-readable storage medium, and loaded and executed by the processor.

For this purpose, some embodiments of the present disclosure provide a non-transitory computer-readable storage medium. The storage medium includes a read-only memory (ROM), a random access memory (RAM), a disk or an optical disc, and the like. Computer programs are stored on the storage medium, and the computer programs, when loaded and run by a processor, cause the processor to perform any of the method for generating the arc treatment plan in the embodiments of the present disclosure. For example, the computer programs, when loaded and run by a processor, cause the processor to:

generating a plurality of sub-regions by partitioning a region of interest based on an irradiation duration corresponding to the region of interest in a target volume; and generating the arc treatment plan for the target volume based on the plurality of sub-regions and irradiation durations corresponding to the plurality of sub-regions;

wherein the irradiation duration corresponding to the region of interest is greater than a predetermined value, the irradiation durations corresponding to the plurality of sub-regions are all less than or equal to the predetermined value, a sum of the irradiation durations corresponding to the plurality of sub-regions is equal to the irradiation duration corresponding to the region of interest, arc ranges corresponding to the plurality of sub-regions are the same as an arc range corresponding to the region of interest, and irradiation positions corresponding to the plurality of sub-regions are the same as an irradiation position corresponding to the region of interest.

In the above embodiments, the description of each embodiment has its own emphasis. The parts not detailed in an embodiment may refer to the detailed description for other above embodiments and are not repeated herein.

In specific implementation, the above various structures are implemented as independent entities, or are arbitrarily combined to be implemented as the same or several entities. The specific implementations of the above various structures may refer to the above method embodiments, and thus are not repeated herein.

The specific implementations of the above various operations may refer to the above embodiments, and thud are not repeated herein.

The method for generating the arc treatment plan, the computer device, and the storage medium in the embodiments of the present disclosure are described in detail herein. Specific examples are used herein to explain the principles and embodiments of the present disclosure. The descriptions of the above embodiments are only used to help understand the method and the core idea of the present disclosure. Meanwhile, those skilled in the art will be changed in the specific embodiments and the application scope according to the idea of the present disclosure. In summary, the content of the Specification should not be understood as a limitation to the present disclosure.

What is claimed is:

1. A method for generating an arc treatment plan, comprising:
   generating a plurality of sub-regions by partitioning a region of interest based on an irradiation duration corresponding to the region of interest in a target volume; and
   generating the arc treatment plan for the target volume based on the plurality of sub-regions and irradiation durations corresponding to the plurality of sub-regions;
   wherein the irradiation duration corresponding to the region of interest is greater than a predetermined value, the irradiation durations corresponding to the plurality of sub-regions are all less than or equal to the predetermined value, a sum of the irradiation durations corresponding to the plurality of sub-regions is equal to the irradiation duration corresponding to the region of interest, arc ranges corresponding to the plurality of sub-regions are the same as an arc range corresponding to the region of interest, and irradiation positions corresponding to the plurality of sub-regions are the same as an irradiation position corresponding to the region of interest.

2. The method according to claim 1, wherein generating the plurality of sub-regions by partitioning the region of interest based on the irradiation duration corresponding to the region of interest in the target volume comprises:
   partitioning the region of interest into a target number of sub-regions with the same irradiation duration based on the irradiation duration corresponding to the region of interest; and
   increasing the target number in response to the irradiation durations corresponding to the plurality of sub-regions being greater than the predetermined value, stopping the partitioning on the region of interest in response to the irradiation durations corresponding to the plurality of sub-regions being less than the predetermined value, and generating the plurality of sub-regions.

3. The method according to claim 2, wherein
   an initial value of the target number is 2; and
   increasing the target number comprises: increasing the target number by 1.

4. The method according to claim 1, wherein generating the plurality of sub-regions by partitioning the region of interest based on the irradiation duration corresponding to the region of interest in the target volume comprises:
   partitioning the region of interest into a plurality of sub-regions with the same irradiation duration based on the irradiation duration corresponding to the region of interest and the predetermined value.

5. The method according to claim 1, wherein upon generating the plurality of sub-regions by partitioning the region of interest based on the irradiation duration corresponding to the region of interest in the target volume, the method further comprises:
   ranking the plurality of sub-regions, and modifying the plurality of sub-regions, such that any two adjacent first sub-region and second sub-region are present in the plurality of sub-regions, wherein an arc stop angle of the first sub-region is an arc start angle of the second sub-region, and an arc direction of the first sub-region is opposite to an arc direction of the second sub-region.

6. The method according to claim 1, wherein generating the plurality of sub-regions by partitioning the region of interest based on the irradiation duration corresponding to the region of interest in the target volume comprises:
   generating the plurality of sub-regions by partitioning the region of interest based on the irradiation duration corresponding to the region of interest in response to an instruction for duplicating the region of interest.

7. The method according to claim 1, further comprising:
   determining whether the irradiation duration corresponding to the region of interest in the target volume is greater than the predetermined value; and
   generating the plurality of sub-regions by partitioning the region of interest based on the irradiation duration corresponding to the region of interest in the target volume comprises:
   generating the plurality of sub-regions by partitioning the region of interest based on the irradiation duration corresponding to the region of interest in response to the irradiation duration corresponding to the region of interest being greater than the predetermined value.

8. The method according to claim 1, wherein generating the plurality of sub-regions by partitioning the region of interest based on the irradiation duration corresponding to the region of interest in the target volume comprises:
generating the plurality of sub-regions by partitioning the region of interest based on the irradiation duration corresponding to the region of interest in response to a partition instruction.

9. The method according to claim 1, wherein generating the plurality of sub-regions by partitioning the region of interest based on the irradiation duration corresponding to the region of interest in the target volume comprises:
generating the plurality of sub-regions by partitioning the region of interest based on the irradiation duration corresponding to the region of interest in response to a treatment plan accept instruction.

10. The method according to claim 1, wherein radiation field sizes corresponding to the plurality of sub-regions are equal to a radiation field size corresponding to the region of interest.

11. The method according to claim 1, wherein the predetermined value is determined based on a minimum rotation speed of a rotating gantry of a radiation device and the arc range corresponding to the region of interest.

12. A computer device, comprising:
one or more processors;
a memory; and
one or more programs stored in the memory;
wherein
the one or more processors, when loading and running the one or more programs, are caused to:
generate a plurality of sub-regions by partitioning a region of interest based on an irradiation duration corresponding to the region of interest in a target volume; and
generate an arc treatment plan for the target volume based on the plurality of sub-regions and irradiation durations corresponding to the plurality of sub-regions;
wherein the irradiation duration corresponding to the region of interest is greater than a predetermined value, the irradiation durations corresponding to the plurality of sub-regions are all less than or equal to the predetermined value, a sum of the irradiation durations corresponding to the plurality of sub-regions is equal to the irradiation duration corresponding to the region of interest, arc ranges corresponding to the plurality of sub-regions are the same as an arc range corresponding to the region of interest, and irradiation positions corresponding to the plurality of sub-regions are the same as an irradiation position corresponding to the region of interest.

13. The computer device according to claim 12, wherein the one or more processors, when loading and running the one or more programs, are caused to:
partition the region of interest into a target number of sub-regions with the same irradiation duration based on the irradiation duration corresponding to the region of interest; and
increase the target number in response to the irradiation durations corresponding to the plurality of sub-regions being greater than the predetermined value, stop the partitioning on the region of interest in response to the irradiation durations corresponding to the plurality of sub-regions being less than the predetermined value, and generate the plurality of sub-regions.

14. The computer device according to claim 12, wherein the one or more processors, when loading and running the one or more programs, are caused to:
partition the region of interest into a plurality of sub-regions with the same irradiation duration based on the irradiation duration corresponding to the region of interest and the predetermined value.

15. The computer device according to claim 12, wherein the one or more processors, when loading and running the one or more programs, are caused to:
rank the plurality of sub-regions, and modify the plurality of sub-regions, such that any two adjacent first sub-region and second sub-region are present in the plurality of sub-regions, wherein an arc stop angle of the first sub-region is an arc start angle of the second sub-region, and an arc direction of the first sub-region is opposite to an arc direction of the second sub-region.

16. The computer device according to claim 12, wherein the one or more processors, when loading and running the one or more programs, are caused to:
generate the plurality of sub-regions by partitioning the region of interest based on the irradiation duration corresponding to the region of interest in response to an instruction for duplicating the region of interest.

17. The computer device according to claim 12, wherein the one or more processors, when loading and running the one or more programs, are caused to:
determine whether the irradiation duration corresponding to the region of interest in the target volume is greater than the predetermined value; and
generate the plurality of sub-regions by partitioning the region of interest based on the irradiation duration corresponding to the region of interest in response to the irradiation duration corresponding to the region of interest being greater than the predetermined value.

18. The computer device according to claim 12, wherein the one or more processors, when loading and running the one or more programs, are caused to:
generate the plurality of sub-regions by partitioning the region of interest based on the irradiation duration corresponding to the region of interest in response to a partition instruction.

19. The computer device according to claim 12, wherein the one or more processors, when loading and running the one or more programs, are caused to:
generate the plurality of sub-regions by partitioning the region of interest based on the irradiation duration corresponding to the region of interest in response to a treatment plan accept instruction.

20. A non-transitory computer readable storage medium, storing one or more computer programs, wherein the one or more computer programs, when loaded and run by a processor, cause the processor to:
generate a plurality of sub-regions by partitioning a region of interest based on an irradiation duration corresponding to the region of interest in a target volume; and
generate an arc treatment plan for the target volume based on the plurality of sub-regions and irradiation durations corresponding to the plurality of sub-regions;
wherein the irradiation duration corresponding to the region of interest is greater than a predetermined value, the irradiation durations corresponding to the plurality of sub-regions are all less than or equal to the predetermined value, a sum of the irradiation durations corresponding to the plurality of sub-regions is equal to the irradiation duration corresponding to the region of interest, arc ranges corresponding to the plurality of sub-regions are the same as an arc range corresponding to the region of interest, and irradiation positions corresponding to the plurality of sub-regions are the same as an irradiation position corresponding to the region of interest.

* * * * *